United States Patent [19]

Gregory

[11] 4,450,852
[45] May 29, 1984

[54] GAS SWITCHING DEVICE

[75] Inventor: Raymond S. Gregory, Bingley, England

[73] Assignee: The Medishield Corporation Limited, London, England

[21] Appl. No.: 334,780

[22] Filed: Dec. 28, 1981

[30] Foreign Application Priority Data

Jan. 6, 1981 [GB] United Kingdom ............... 8100216

[51] Int. Cl.³ .......................................... G01L 19/12
[52] U.S. Cl. ..................................... 137/114; 137/557
[58] Field of Search ............... 137/109, 114, 557; 60/421, 422

[56] References Cited

U.S. PATENT DOCUMENTS

| | | | |
|---|---|---|---|
| 3,987,704 | 10/1976 | Johnson | 60/421 |
| 4,073,141 | 2/1978 | Lohbauer | 60/421 |
| 4,345,436 | 8/1982 | Johnson | 60/422 |
| 4,350,115 | 9/1982 | Pasternack | 137/557 |

Primary Examiner—Martin P. Schwadron
Assistant Examiner—James R. Shay

Attorney, Agent, or Firm—Roger M. Rathbun; Larry R. Cassett

[57] ABSTRACT

A gas switching device for use with a gas supply system in which two gases, for example, oxygen and air are supplied to a medical unit comprises a manifold 106 to which are attached two identical valve assemblies 108, 110. The manifold has a first inlet 1 and outlet 5 for the passage therethrough of the oxygen and a second inlet 2 and outlet 6 for the air. Each valve assembly 108, 110 includes a spool valve 122 movable from a first to a second position under the influence of the pressure of its associated gas. At least one valve assembly 110 has an inlet 18' communicating with a passageway 15 in the manifold which, in turn, communicates with the inlet 1 for the oxygen and an outlet 22 communicating with a further passageway 16 in the manifold which in turn communicates with the outlet 6 in the manifold for the air. Should the air pressure drop below a predetermined value then spool valve 122 will move to its second position thereby permitting the passage of oxygen from inlet 18' to the outlet 22 in the valve assembly 110 so that oxygen exits from both outlet 5 and outlet 6.

9 Claims, 6 Drawing Figures

GAS SWITCHING DEVICE

FIELD OF THE INVENTION

The present invention relates to gas switching devices for use in gas supply systems in which first and second gases are each supplied from a source to a unit at a predetermined pressure and in particular, to gas switching devices for use in gas supply systems in which first and second gases, for example, oxygen and air are each supplied from a source to a medical unit such as a medical gas mixer.

BACKGROUND OF THE INVENTION

It is known to supply air and oxygen each from separate sources to a medical gas mixer where the air and oxygen are mixed in a predetermined ratio for delivery to a patient. Should the air supply fail, that is, the air pressure fall below a predetermined level, then the mixer will cut out without warning and no gases will flow to the patient.

If the oxygen supply fails the mixer continues to deliver to the patient only the set air flow so that the total flow of gas reaching the patient can drop.

This is unsatisfactory since it can be dangerous to the health of the patient should the flow rate of gases reaching him suddenly change or cease especially if this is not noticed immediately and alternative means of gas supply have to be found and connected.

AIM OF THE INVENTION

It is an aim of the invention to provide a gas switching device which will eliminate or minimise the disadvantage referred to above.

SUMMARY OF THE INVENTION

According to one aspect of the present invention, a gas switching device for use with a gas supply system in which first and second gases are each supplied from a source to a unit at a predetermined pressure, the device being positioned upstream of the unit, comprises a manifold having a first inlet and outlet for the passage therethrough of the first gas and a second inlet and outlet for the passage the through of the second gas, a first valve assembly associated with the first gas and a second valve assembly associated with the second gas, each valve assembly including a member movable from a first to a second position under the influence of the pressure of its associated gas at its inlet to the manifold, each valve assembly having an inlet communicating with a passageway in the manifold which, in turn, communicates with the inlet of the manifold for the other gas, and an outlet spaced from said inlet, said outlet communicating with a second passageway in the manifold which, in turn, communicates with the outlet in the manifold for the associated gas, the arrangement being such that whilst the predetermined pressures of the first and second gases are maintained, the members each occupy the first position thereby isolating each valve assembly inlet from its outlet, but if the pressure of one gas should drop below its predetermined value, then the member of the valve assembly associated with that gas will move to its second position thereby permitting the passage of the other gas from the inlet to the outlet of that valve assembly so that said other gas exits from the first and second outlets of the manifold.

A particular advantage of the gas switching device defined above is that should the pressure of any one of the gases drop below its predetermined value the other gas will flow out of both outlets to the downstream unit and enable it to continue to operate at substantially unchanged total flow.

According to a further aspect of the present invention, a gas switching device for use with a gas supply system in which first and second gases are each supplied from a source to a unit at a predetermined pressure, the device being positioned upstream of the unit, comprises a manifold having a first inlet and outlet for the passage therethrough of the first gas and a second inlet and outlet for the passage therethrough of the second gas, a first valve assembly associated with the first gas and a second valve assembly associated with the second gas, each valve assembly including a member movable from a first to a second position under the influence of the pressure of its associated gas at its inlet to the manifold, the second valve assembly having an inlet communicating with a passageway in the manifold in which in turn communicates with the inlet of the manifold for the first gas, and an outlet spaced from said inlet, said outlet communicating with a second passageway in the manifold which, in turn communicates with the outlet in the manifold for the second gas, the arrangement being such that whilst the predetermined pressures of the first and the second gases are maintained, the members each occupy the first position thereby isolating each valve assembly inlet from its outlet, but if the pressure of the second gas should drop below its predetermined value then the member of the second valve assembly will move to its second position thereby permitting the passage of the first gas from the inlet to the outlet of said second valve assembly so that said first gas exits from the first and the second outlets of the manifold.

A particular advantage of the gas switching device defined above is that the device can be used to supply medical gases to a medical unit where the second gas is, on its own, incapable of supporting life.

BRIEF DESCRIPTION OF DRAWINGS

An embodiment of the invention will now be described, by way of example, reference being made to the Figures of the accompanying diagrammatic drawings in which.

DESCRIPTION OF PREFERRED EMBODIMENT

Figure 1:
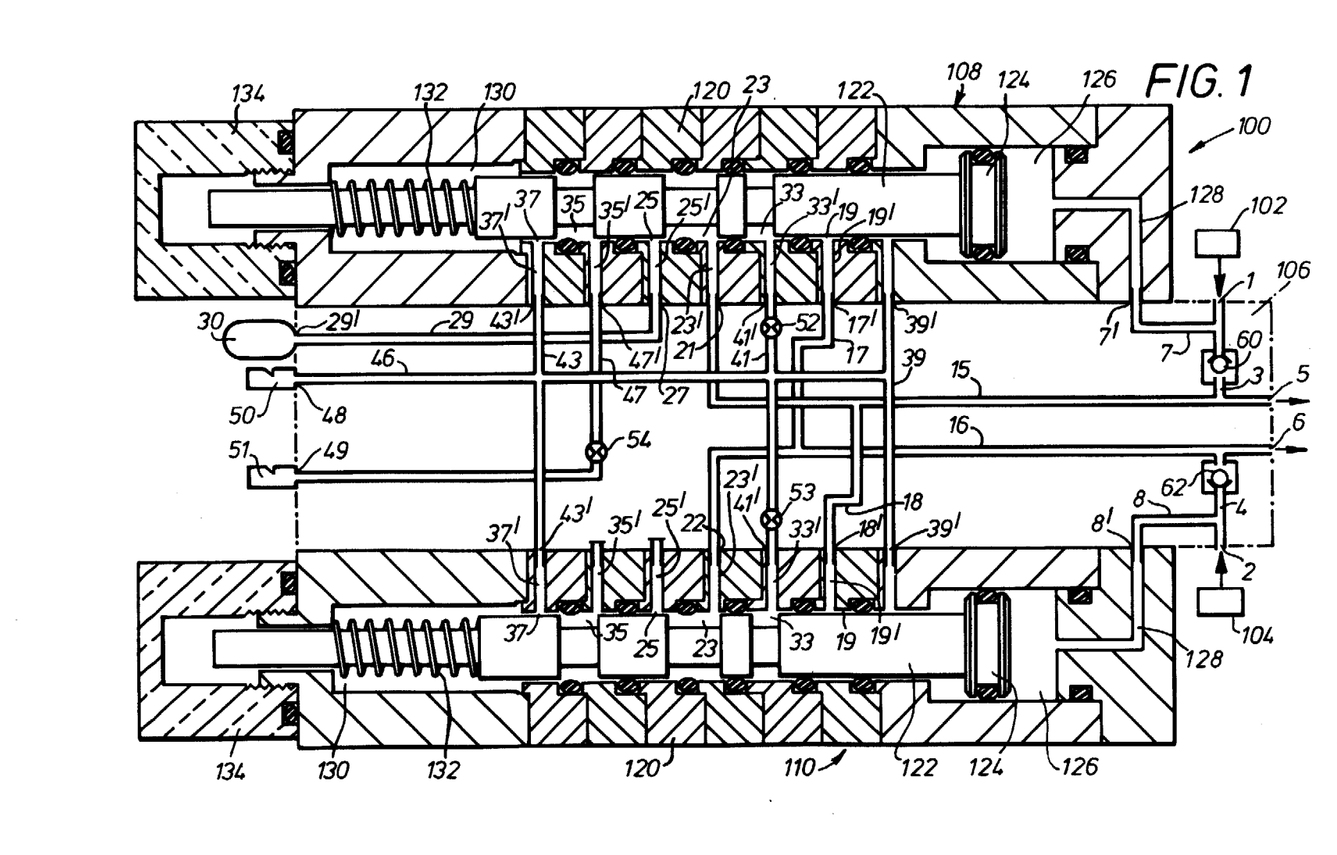
FIG. 1 is a schematic view partly in cross-section of a gas switching device with first and second gases being supplied to the device at predetermined pressures.

As shown, a gas switching device 100 for use with a gas supply system in which first and second gases each supplied respectively from a source 102 and a source 104 at a predetermined pressure comprises a manifold 106, a first valve assembly 108 and a second valve assembly 110. The manifold 106 is in the form of a block having opposed upper and lower sides (as shown), a right-hand end and a left-hand end. The first valve assembly 108 is attached by means not shown to the upper side of the manifold 106 and the second valve assembly 110 is attached by means not shown to the opposite lower side of the manifold 106.

The manifold 106 has a first inlet 1 for the first gas, for example, oxygen from the source 102. Inlet 1 communicates with a passageway 3 in which is located a one-way valve 60. From the valve 60, the passageway 3 meets a passageway 15 which in a first direction extends to a first outlet 5 at the right-hand end of the manifold 106 and in the opposite direction leads to a port 21 on the upper (as shown) side of the manifold 106. Between the ends of the passageway 15 in a junction at which a passageway 18 communicates with the passageway 15. The passageway 18 leads to a port 18' on the lower side of the manifold 106. A passageway 7 extends from a port 7' on the upper side of the manifold 106 to a junction with the passageway 3 between the inlet 1 and the one-way valve 60.

Similarly, the manifold 106 has a second inlet 2 for the second gas, for example, air from the source 104. Inlet 2 communicates with a passageway 4 in which is located a one-way valve 62. From the valve 62, the passageway 4 meets a passageway 16 which in a first direction leads to a second outlet 6 at the right-hand end of the manifold 106 and in the opposite direction leads to a port 22 on the lower side of the manifold 106. Between the ends of the passageway 16 is a junction at which a passageway 17 communicates with the passageway 16. The passageway 17 leads to a port 17' on the upper side of the manifold 106. A passageway 8 extends from a port 8' on the lower side of the manifold 106 to a junction with the passageway 4 between the inlet 2 and the one-way valve 62.

Three spaced passageways 39, 41 and 43 extend from the upper to the lower side of the manifold 106 and respectively intercommunicate ports 39', 41' and 43' on said upper and lower sides of the manifold. The passageways 39, 41, and 43 are in turn connected by a passageway 46 leading to a port 48 at the left-hand end of the manifold 106. The port 48 communicates with an audible warning device 50 attached to the left-hand end of the manifold 106. Two bleed valves 52, 53 are positioned in the passageway 41 one on each side of the junction with the passageway 46.

Another passageway 47 extends from a port 47' on the upper side of the manifold 106 to a port 49 on the left-hand end of the manifold. The port 49 is in connection with yet a further audible warning device 51. A bleed valve 54 is located in the passageway 47.

Finally, a further passageway 29 extends from a port 27 on the upper side of the manifold 106 to a port 29' on the left-hand end of the manifold which port 29' communicates with the interior of an acculator 30 arranged externally of the manifold.

The valve assemblies 108 and 110 are of conventional design and substantially identical. For convenience, only the first valve assembly 108 will be referred to in any detail by way of explaining its structure and function. Like reference numerals will be used to identify the like parts of the valve assemblies 108, 110.

The valve assembly 108 comprises a main body 120 accommodating movable member in the form of a spool valve 122. At its right-hand end (as shown) the spool valve 122 carries a piston 124 movable in a cylinder 126 formed in the body 120. A passage 128 in the body 120 extends from the cylinder 126 to communicate with the port 7' in the manifold 106. In the case of valve assembly 110, the passage 128 extends from the cylinder 126 to the port 8' on the lower side of the manifold 106.

A chamber 130 at the left-hand end of the body 120 containes resilient means in the form of a coil spring 132 which biases the spool valve 122 and hence the piston 124 towards the right-hand end of cylinder 126. The far left-hand end of the body 120 has attached to it a transparent or translucent cap 134.

Intermediate the ends of the spool valve 122 there are in a manner known, a plurality of spaced, enlarged diameter portions which together with the body 120 define between them a plurality of chambers 19, 33, 23, 25, 35 and 37. It will be clear that according to the position of the spool valve 122 within the body 120 will depend which, if any, of the chambers can communicate with each other. The chambers are isolated by sealing means known in the valve art. Each chamber has a corresponding passage which extends from its associated chamber to a port on the upper side of the manifold 106. Hence, chamber 19 has associated with it a passage 19' which communicates with port 17'; chamber 33 has a passage 33' associated with it which communicates with the port 41'; chamber 23 has a passage 23' associated with it which communiates with the port 21; chamber 25 has a passage 25' associated with it which communicates with the port 27; chamber 25 has a passage 35' which communicates with the port 47'; and chamber 37 has a passage 37' associated with it which communicates with the port 43'.

It should be noted that in the case of the valve assembly 110 the passages 25' and 35' leading respectively from chambers 25 and 35 are blanked off.

In use, the device 100 is positioned upstream of a medical unit such as a medical gas mixer or flow meter. If the pressures of the first and second gases are within predetermined limits, then a major porton of the first gas oxygen will flow from the source 102 through the first inlet 1 into the passage 3 through the one-way valve 60 and into passage 15 where it will leave the manifold 106 via the first outlet 5. However, some of the oxygen will flow along the passageway 7 through the port 7' and into the passage 128 in the body 120 of the first valve assembly 108 and hence into the cylinder 126. The oxygen will exert a pressure on the piston 124 against the bias of its spring 132. In this situation, the piston 124 and spool valve 122 will occupy the positions shown in FIG. 1. Further, some oxygen will also flow along the passage 15 to port 21, passage 23' and into chamber 23. In the position of the spool valve 122 illustrated in FIG. 1, chambers 23 and 25 are in communication so that the oxygen will then flow through chamber 25, passage 25', port 27, passageway 29, port 29' and into the accumulator 30.

Also, some oxygen will flow via passagway 18, port 18', passage 19' and into chamber 19 of the valve assembly 110.

Similarly, a major portion of the second gas air will flow from source 104 through the second inlet 2 into the passageway 4 through the one-way valve 62 into passageway 16 where it will leave the manifold 106 via the second outlet 6. Some of the air will flow along passageway 8 through port 8' into passage 128 in the second valve assembly 110 and into the cylinder 126 where it will exert pressure on the piston 124 against the bias of spring 132. Again, in this situation, the piston 124 and spool valve 122 of the valve assembly 110 will occupy the positions shown in FIG. 1.

Some air will also flow along the passage 16 to port 22, passage 23' into chamber 23 in the valve assembly 110. In the illustrated position of the spool valve 122 chambers 23 and 25 are in communication so that the air will flow through into chamber 25 and passage 25' but will flow no farther since passage 25' in the valve assembly 110 is blanked off.

Further, some air flows via passageway 17, port 17' and passage 19' into chamber 19 of the valve assembly 108.

Figure 2:
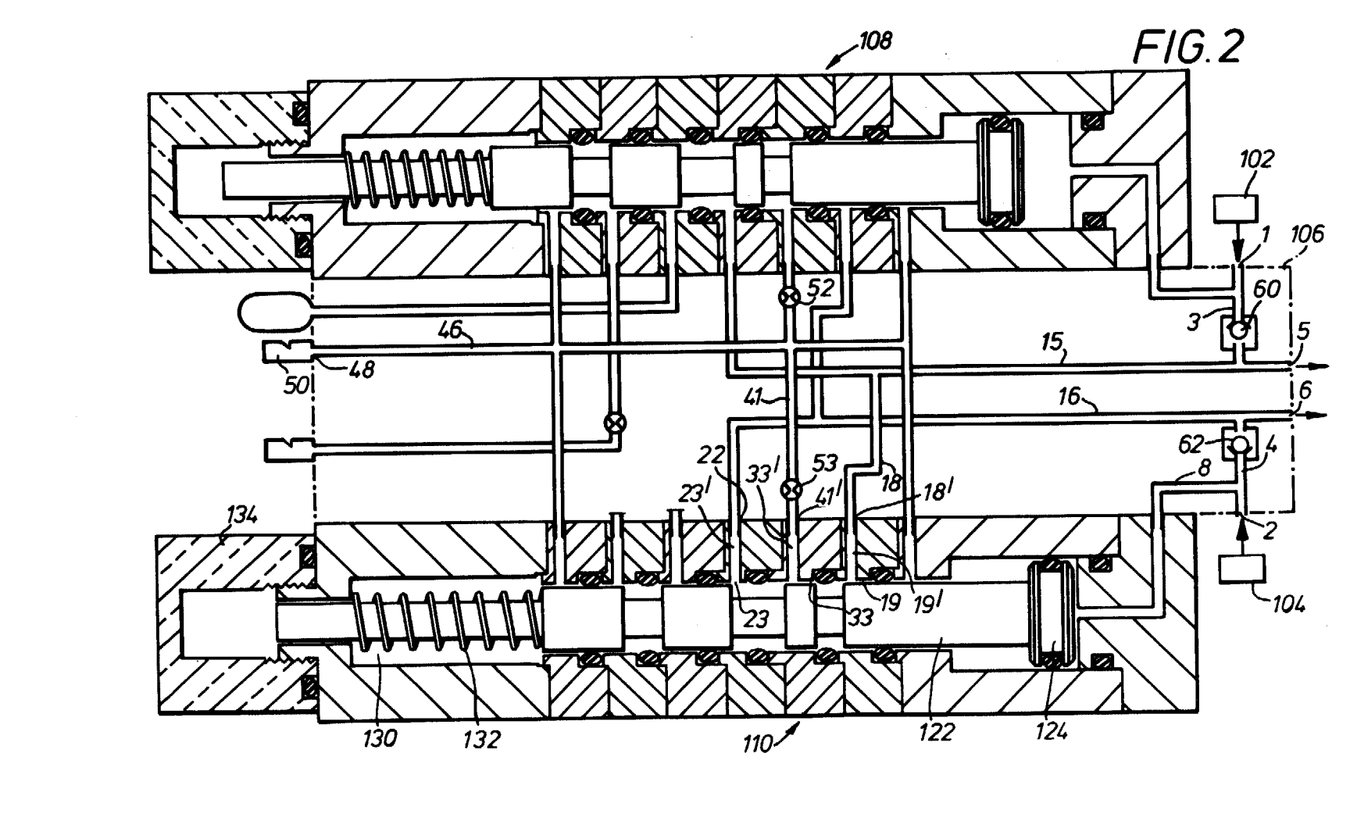
FIG. 2 is a view similar to FIG. 1 except that the pressure of the second gas has failed and the member of the valve assembly associated with the second gas is shown in its second position.

If we take the situation where the pressure of the air, for example, were to fall below a predetermined level, this would have the effect of permitting the spring 132 in the valve assembly 110 to force the spool valve 122 and piston 124 towards the right to occupy the positions illustrated in FIG. 2. In the positions occupied by the spool valve and piston 124 illustrated in FIG. 2 then the oxygen will not only follow the paths already indicated when the pressures of the oxygen and air are within their predetermined limits but will also flow via passageway 18, port 18', passage 19', chamber 19 and from chamber 19 into chambers 33 and 23. From chamber 23 the oxygen then flows via passage 23' via port 22 and through the passageway 16 to the second outlet 6.

The oxygen thus flows out of both first and second outlets 5, 6 to the downstream unit and enables it to continue to operate at a substantially unchanged total flow.

The presence of the non-return valve 62 ensures that the pressure of oxygen does not reach passageway 4 or the cylinder 126 of valve assembly 110 to reactivate the valve assembly 110. If the loss of air is due to a hose or component failure opening the inlet line to the manifold to atmosphere the nonreturn valve 62 ensures that oxygen does not also escape in the same way.

To ensure that a warning is given that this situation has occurred some of the oxygen that flows into chamber 33 will exit via passage 33' to port 41' where it flows through bleed valve 53 and passageways 41 and 46 to reach the port 48 and operate the audible warning device 50. Confirmation that the air has failed can be obtained by visual observation of the left-hand end of the spool valve 122 through the transparent or translucent cap 134.

If the oxygen were to fail a similar situation would apply to the valve assembly 108 and air would flow through both the first and second outlets 5, 6, audible warning being given by some of the air venting through the bleed valve 52 and flowing via the passageway 46 and port 48 to the audible warning device 50.

Figure 3:
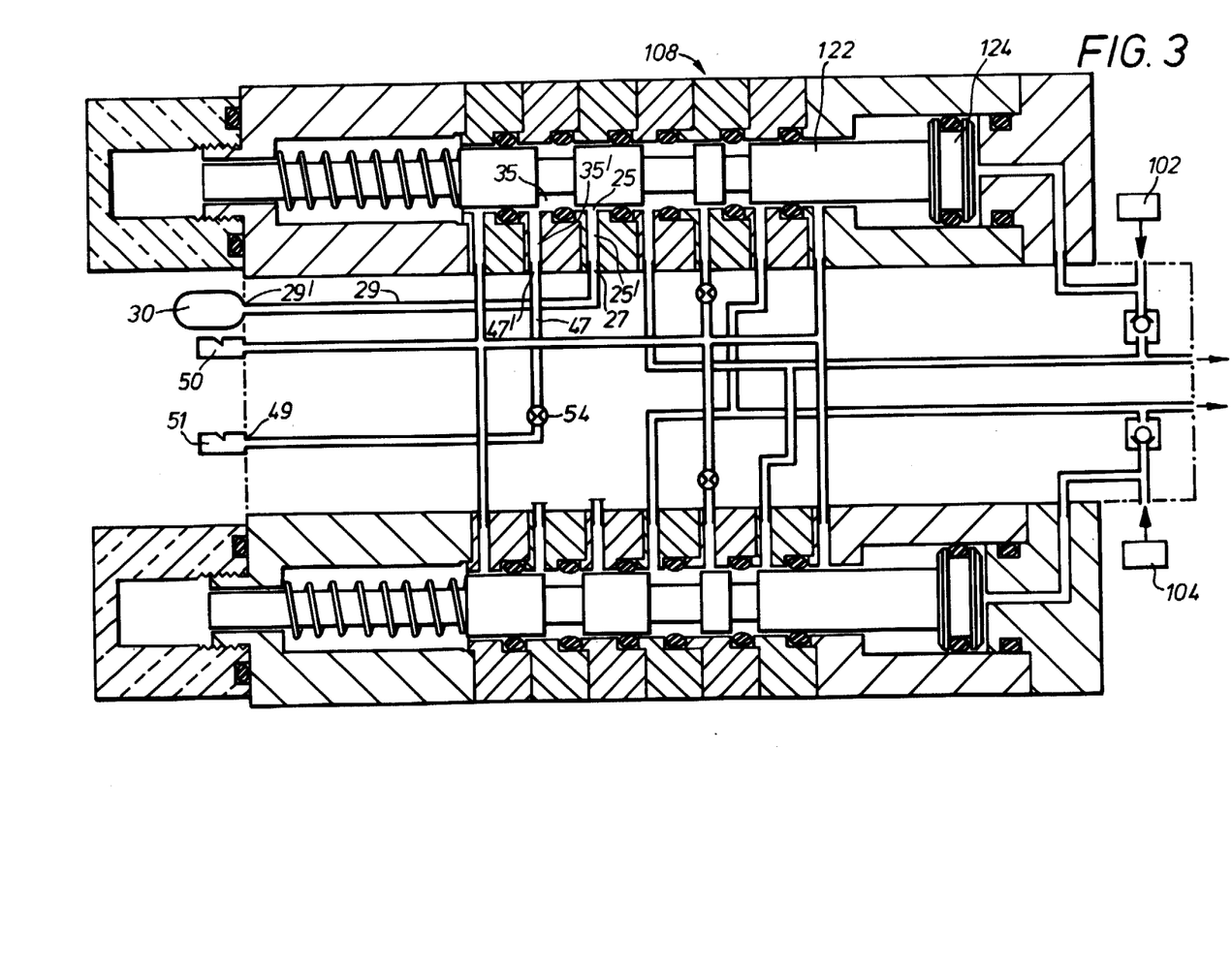
FIG. 3 is a view similar to FIGS. 1 and 2 but illustrates the position of the members of each valve assembly when both gases have failed to reach predetermined pressure levels.

It is a requirement of a number of national standards that when oxygen is supplied to a unit it must be the oxygen that powers an alarm when it is the oxygen supply which fails. It will be seen from FIG. 3 that should the oxygen fail then the piston 124 and spool valve 122 of the valve assembly 108 would occupy the position shown which will enable oxygen in the accumulator 30 to flow via port 29', passageway 29, port 27 and passage 25' into chamber 25. From chamber 25 the oxygen will then be able to flow into chamber 35, passage 35', passageway 47, through the bleed valve 54 to the port 49 and audible warning device 51. It will be understood that the tone or quality of the audible warning device 51 should be different from that of the audible warning device 50.

Figure 4:
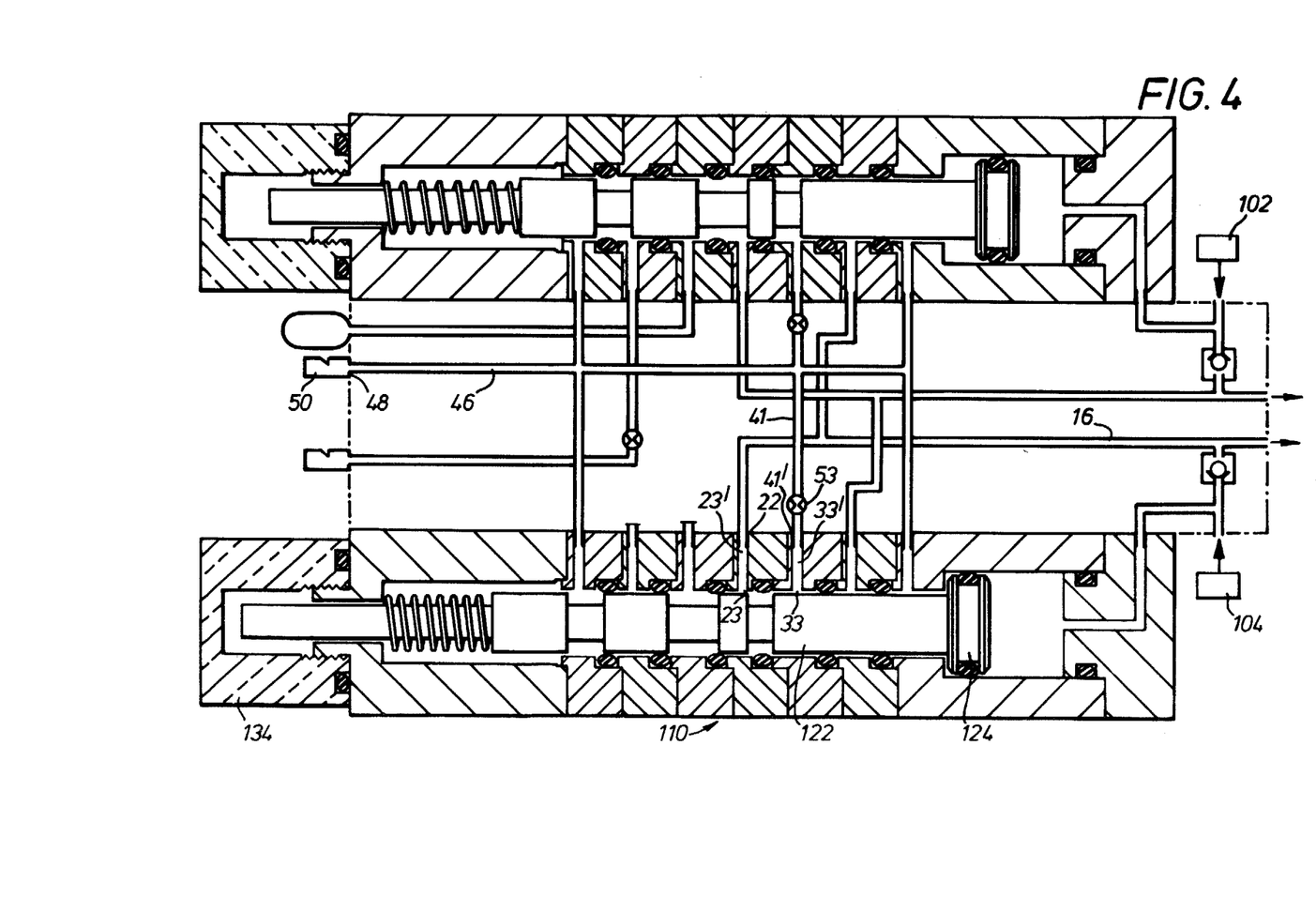
FIG. 4 is a view similar to FIGS. 1, 2 and 3 but illustrates the position of the member of the valve assembly associated with the second gas when said second gas is delivered to the device at above a predetermined pressure.

Turning now to FIG. 4, this illustrates the position of the spool valve 122 and piston 124 of the valve assembly 110 when the air is being supplied at too high a pressure. This can happen, for example, when compressed air cylinder regulators ae set at the wrong pressure or where compressed air supplies in a hospital are available at pressures of 4 bars and 7 bars and the wrong connection is made. It will be seen that the high pressure of the air will force the piston 124 of the valve assembly 110 towards the left allowing air to flow from chamber 23 to chamber 33 out from port 41' and through bleed valve 53 into the passageway 41 and hence via passageway 46, port 48 through the audible warning device 50 to provide said audible warning. A visual observation of the left-hand end of the spool valve 122 through the cap 134 will permit of a confirmation that it is a high pressure alarm which is being given.

To summarise the actions of the device 100 when failure is occurring in the gas supply:

If the first gas (oxygen) fails then a short audible warning from audible warning device 51 will occur plus a continuous alarm from audible warning device 50 plus a connection of the second gas (air) to the first outlet 5 plus a visual confirmation.

If the second gas (air) fails then a continuous alarm from audible warning device 50 will occur plus a connection of the first gas oxygen to the second gas outlet 6 plus a visual confirmation.

If both gases fail then a short audible warning will be heard from the device 51 and a visual confirmation will be given.

If the first or second gases are supplied at too high a pressure, then a continuous alarm from audible warning device 50 will occur plus a visual confirmation.

A number of modifications can be made to the embodiment of gas switching device described above. For example, in place of the coil springs illustrated a stack of Bellville washers or disc springs can be used. Whatever types of springs are used it is preferable if the spring rate of the springs is non-linear and is arranged so that the pistons 124 are preloaded at one extreme position until the gas pressure rises to a predetermined minimum level suitable for satisfactory operation of the unit being supplied with the gases. At this minimum level the force on the spool valve 122 is sufficient to compress the springs at a low spring rate until the valve spools have moved to the normal operating position shown in FIG. 1. It is desirable that the spring should then have a very high stiffness, minimising valve movement as the pressure increases over the working range until a second predetermined maximum pressure is reached at which the resultant load on the spool valve and hence on the springs will have risen to a point where the spring rate is again relatively low causing a rapid movement of the spools to the second extreme position.

A single bleed valve could be used in the passaveway 41 if both the ports 41' were interconnected before the valve, with a single connection then being made to passageway 46.

Figure 5:
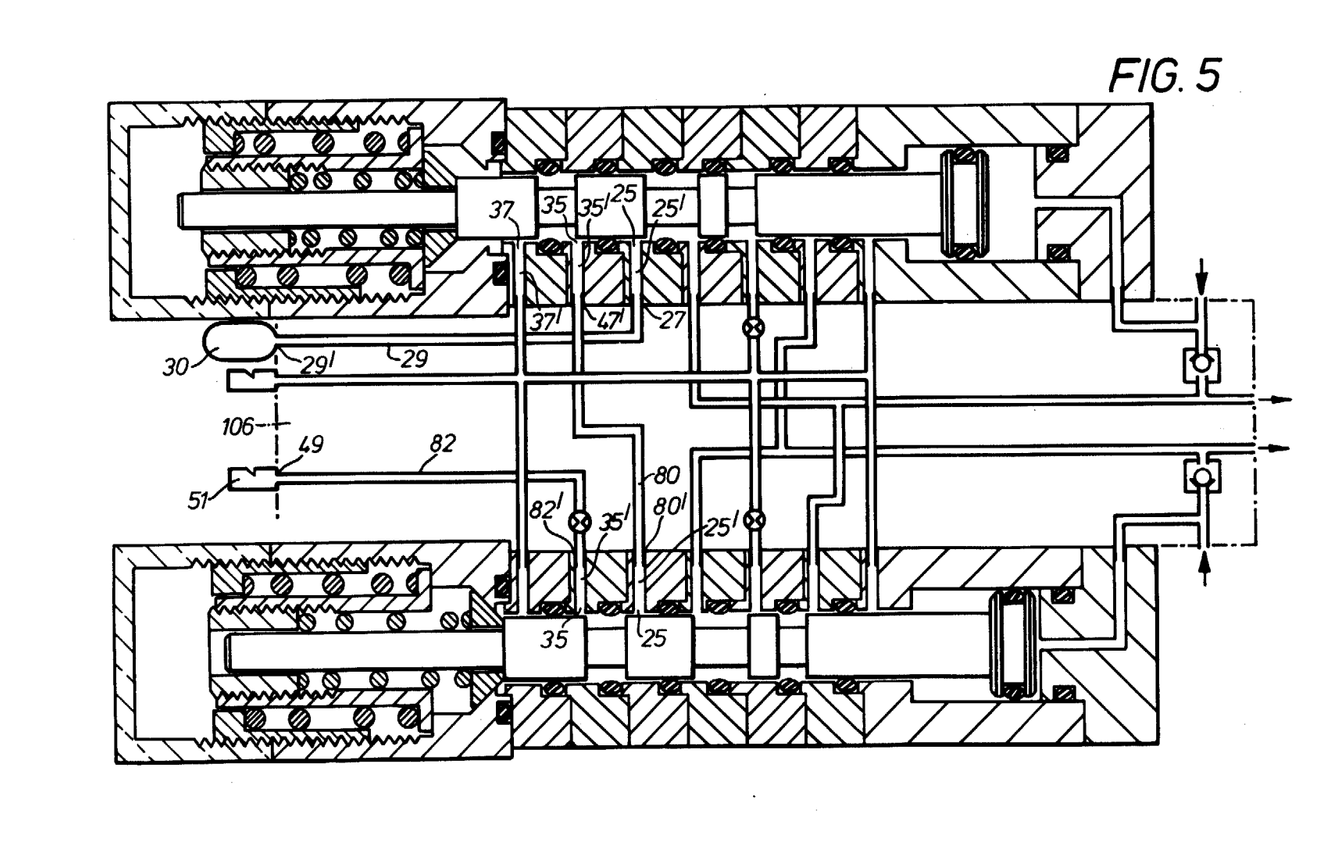
FIG. 5 is a view similar to FIGS. 1 to 4 but illustrating a modification of the device.

FIG. 5 illustrates a modification in the manifold 106 which provides an alternative way of connecting the accumulator 30 to the audible warning device 51.

As before accumulator 30 is connected to the left-hand end of the manifold 106 and communicates with port 29'. From port 29', the passageway 29 leads to the port 27 on the upper side of the manifold 106. Passage 25' leads to chamber 25 and when the pressure of oxygen falls below a predetermined value, chamber 25 will communicate with chamber 35. Hence, oxygen in the accumulator 30 will flow from chamber 35, passage 35' to port 47' and from port 47' through passageway 80 to port 80' on the lower side of the manifold 106. From port 80' the oxygen wil flow through passage 25' to chamber 25 and when the pressure of the air is below a predetermined minimum, from chamber 25 to chamber 35, passage 35', port 82', passageway 82 to port 49 and audible warning devvice 51.

Figure 6:
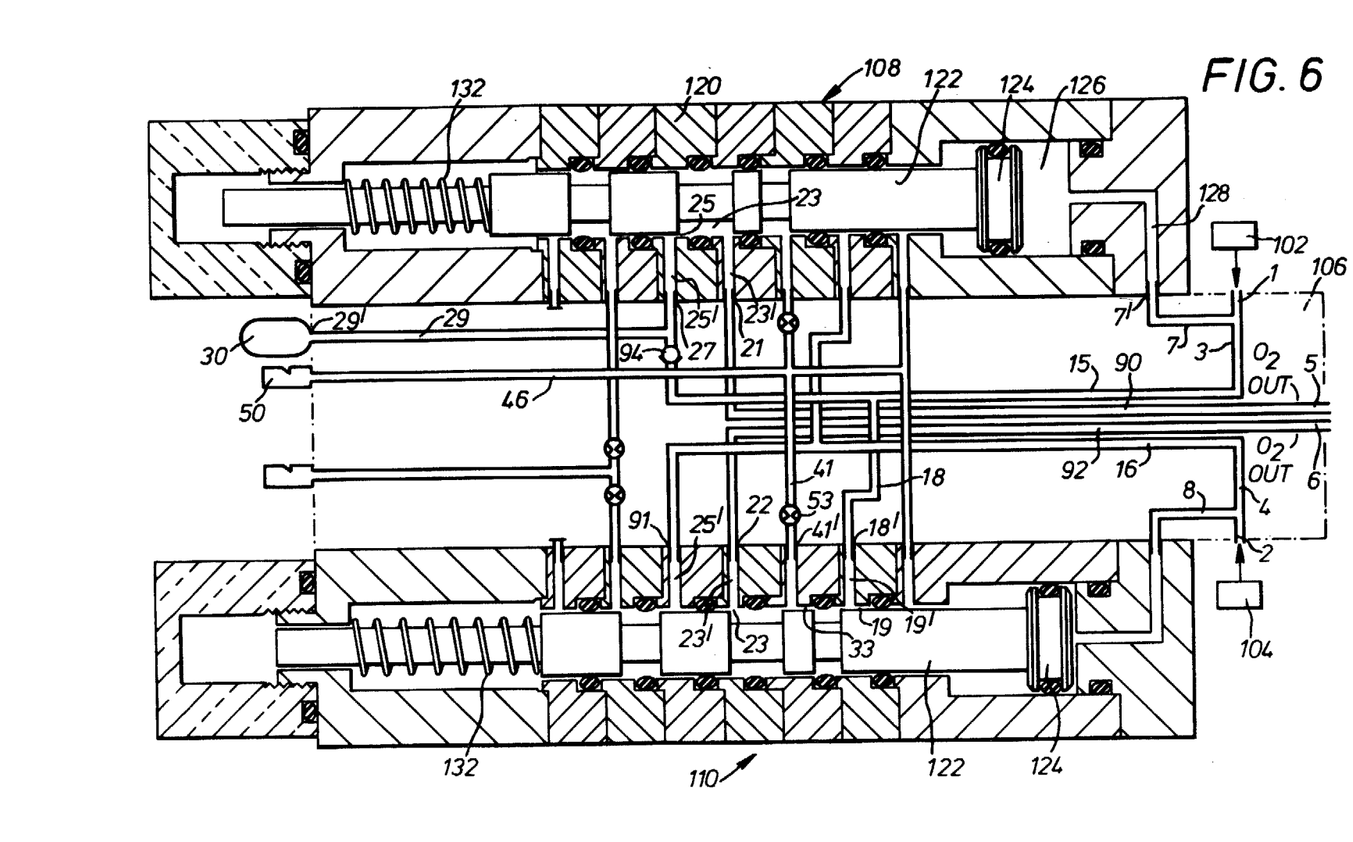
FIG. 6 is a view similar to FIGS. 1 to 4 but illustrating yet a further modification of the device.

It will be apparent that with this arrangement the device 51 will only operate when the pressures of both gases falls below the predetermined levels. FIG. 6 illustrates yet a further modification of the manifold 106. Passageway 15 now extends from passageway 3 to port 27 in the first valve assembly 108 and port 21 communicates with a new passageway 90 which leads to first outlet 5. Similarly, passageway 16 now extends from the passageway 4 to port 91 in the second valve assembly 110, the blanking piece on passage 25' now having been removed and port 22 communicates with a new passageway 92 which leads to second outlet 6. A non-return valve 94 is positioned in passageway 15 and passageway 29 from the accumulator 30 communicates with passageway 15 at a location between the valve 94 and port 27.

In use, if the supply of air fails, that it, the presence of the air falls below a predetermined level, then spring 132 in the valve assembly 110 will force spool valve 122 and piston 124 towards the right to occupy the positions illustrated in FIG. 6. In the positions occupied by the spool valve and piston in FIG. 6, then oxygen will flow as follows:

1. From passageway 3 to passageway 7, through port 7' and into the passage 128 in the body 120 of the first valve assembly 108 and hence into the cylinder 126. The oxygen will exert a pressure on the piston 124 against the bias of its spring 132 so that the piston 124 and spool valve 122 occupy the position shown in FIG. 6.

2. From passageway 3 along passageway 15 and past on-way valve 94, most of the oxygen will flow to port 27 then along passageway 25' to chamber 25 and from chamber 25 to chamber 23. From chamber 23 the oxygen will flow along passage 23' to port 21 and hence along passageway 90 to the first outlet 5. Some of the oxygen will flow from the passageway 15 and along passageway 29, port 29 and into the accumulator 30.

3. From passageway 3 and passageway 15 along passageway 18 to port 18'. Along passage 19' and chamber 19 to chambers 33 and 23 from whence the oxygen flows along 23' to port 22. From port 22 the oxygen flows along passageway 92 to second outlet 6. Some of the oxygen from chamber 33 will flow along passage 33' to port 41' and hence along passageways 41 and 46 to operate the audible warning device 50. This arrangement dispenses with the non-return valves 60, 62. In practice, it is difficult to guarantee that the valves 60, 62 will be leak proof and if, for example, valve 62 leaks and there is a blockage in the line from the source 104 of air to the inlet 2 then pressure can slowly build up in the passageway 8 and passage 128 until the spool valve 122 of the valve assembly 110 is re-activated and moved to the left (as shown) until it occludes port 18'. There is a need to place a non-return valve 94 in the passageway 15 but this is relatively non-critical since small leaks would not affect operation significantly.

A further advantage of the arrangement of the chambers in valve assemblies 108, 110, is that when the valves are in the first position any chamber pressurised by the first gas is always separated by an intermediate chamber from any chambers pressurised by the second gas. Since the intermediate chambers are vented to atmosphere via the audible alarm any gas which leaks across a faulty seal with be vented and will not contaminate the other gas supply. A sizeable leak would result in an audible warning being given.

While reference has been made in the above described embodiment to oxygen and air as the gases being supplied to a medical gas mixer, other gases or gas mixtures, each capable of supporting life, can be used. For example, a gas mixture of equal parts nitrous oxide and oxygen can replace the air of the above described embodiment. When operation with a gas incapable of supporting life on its own is desired then the device can be used but the cross-connecting passageway for that gas between the valve assemblies must not be used and should be blanked-off. For example, if nitrous oxide were used in place of air as per the above described embodiment then passageway 17 must be blanked-off.

The valve assemblies 108 and 110 are as previously explained conventional and this has resulted in certain chambers being redundant for the purposes explained above. However, the use of common valve assemblies of conventional design simplifies stock keeping and spare part requirements.

I claim:

1. A gas switching device for use with a gas supply system in which first and second gases are each supplied from a source to a unit at a predetermined pressure, the sevice being positioned upstream of the unit and comprising a manifold having a first inlet and outlet for the passage therethrough of the first gas and a second inlet and outlet for the passage therethrough of the second gas, a first valve assembly associated with the first gas and a second valve assembly associated with the second gas, each valve assembly being operable independently of the other valve assembly and including a member movable from a first to a second position under the influence of the pressure of its associated gas at its inlet to the manifold, each valve assembly having an inlet communicating with a passageway in the manifold which, in turn, communicates with the inlet of the manifold for the other gas, and an outlet spaced from said inlet, said outlet communicating with a second passageway in the manifold which, in turn, communicates with the outlet in the manifold for the associated gas, the arrangement being such that whilst the predetermined pressures of the first and the second gases at each respective inlet to the manifold are maintained, the members each occupy the first position thereby isolating each valve assembly inlet from its outlet, but if the pressure of one gas from its source should drop below its predetermined value then the member of the valve assembly associated with that gas will move to its second position thereby permitting the passage of the other gas from the inlet to the outlet of that valve assembly so that said other gas exits from the first and the second outlets of the manifold to maintain the total flow of gas from the switching device substantially constant.

2. A device as claimed in claim 1, in which the first and second inlets each communicate with one of a first pair of passageways in the manifold which in turn each communicate with one of a second pair of passageways in the manifold, each passageway of the second pair extending between an outlet from the manifold and an outlet from an associated valve assembly, each passageway of the first pair accommodating a non-return valve, and a third pair of passageways in the manifold each extending respectively from a passageway of the second pair to an inlet of an associated valve assembly.

3. A device as claimed in claim 1 in which the first and second inlets each communicate with one of a first pair of passageways in the manifold which in turn each communicate with one of a second pair of passageways in the manifold, each passageway of the second pair communicates with a second inlet in its associated valve assembly which in the first position of the member communicates with the outlet of the valve assembly and a third pair of passageways in the manifold, each passageway of the the third pair extending from an outlet in a respective valve assembly to an outlet in the manifold.

4. A device as claimed in claim 1 in which means are provided for detecting said pressure drop in said one gas and actuating a warning device.

5. A device as claimed in claim 4 in which the detecting and actuating means includes a bore in the valve assembly which, when the member moves to its second position, allows a proportion of the other gas to pass therethrough and into a bore in the manifold communicating with an audible warning device.

6. A device as claimed in claim 1, in which one valve assembly includes a second inlet and a second outlet spaced from said second inlet, said second inlet communicating with a source of gas under pressure and said second outlet communicating with a passageway in the manifold which, in turn, communicates with a further audible warning device, the arrangement being such that when the member is in its first position, the second inlet is isolated from the second outlet but should the member move to its second position then the gas from the source is permitted to flow to the second outlet and actuate the audible warning device.

7. A device as claimed in claim 1, in which the member of each valve assembly is movable to a third position under the influence of the pressure of the gas associated with the valve assembly at its inlet to the manifold when the gas pressure rises above a predetermined value and in which means are provided for detecting said rise in the gas pressure and actuating a warning device.

8. A device as claimed in claim 7, in which the detecting and actuating means includes a bore in the valve assembly in which when the member moves to its third position allows a proportion of the gas to pass therethrough and into a bore in the manifold communicating with an audible warning device.

9. A gas switching device for use with a gas supply system in which first and second gases are each supplied from a source to a unit at a predetermined pressure, the device being positioned upstream of the unit and comprising a manifold having a first inlet and outlet for the passage therethrough of the first gas and a second inlet and outlet for the passage therethrough of the second gas, a first valve assembly associated with the first gas and a second valve assembly associated with the second gas, each valve assembly being operable independently of the other valve assembly and including a member movable from a first to a second position under the influence of the pressure of its associated gas at its inlet to the manifold, the second valve assembly having an inlet communicating with a passageway in the manifold which, in turn, communicates with the inlet of the manifold for the first gas, and an outlet spaced from said inlet, said outlet communicating with a second passageway in the manifold which, in turn, communicates with the outlet in the manifold for the second gas, the arrangement being such that whilst the predetermined pressures of the first and the second gases at each respective inlet to said manifold are maintained, the members each occupy the first position thereby isolating each valve assembly inlet from its outlet, but if the pressure of the second gas from its source should drop below its predetermined valve then the member of the second valve assembly will move to its second position thereby permitting the passage of the first gas from the inlet to the outlet of said second valve assembly so that said first gas exists from the first and the second outlets of the manifold to maintain the total flow of gas from the switching device substantially constant.

* * * * *